US008298288B2

(12) United States Patent
Walker

(10) Patent No.: US 8,298,288 B2
(45) Date of Patent: Oct. 30, 2012

(54) RECESS-RAMP KNEE JOINT PROSTHESIS

(75) Inventor: Peter Stanley Walker, New York, NY (US)

(73) Assignee: New York University, New York, NY (US)

( * ) Notice: Subject to any disclaimer, the term of this patent is extended or adjusted under 35 U.S.C. 154(b) by 305 days.

(21) Appl. No.: 12/489,288

(22) Filed: Jun. 22, 2009

(65) Prior Publication Data

US 2009/0319047 A1  Dec. 24, 2009

Related U.S. Application Data

(60) Provisional application No. 61/075,158, filed on Jun. 24, 2008, provisional application No. 61/100,488, filed on Sep. 26, 2008.

(51) Int. Cl.
*A61F 2/38* (2006.01)

(52) U.S. Cl. .................. 623/20.21; 623/20.31

(58) Field of Classification Search .......... 623/20.14, 623/20.15, 20.27, 20.31
See application file for complete search history.

(56) References Cited

U.S. PATENT DOCUMENTS

| | | | |
|---|---|---|---|
| 4,963,152 A * | 10/1990 | Hofmann et al. ........ | 623/20.31 |
| 5,330,533 A | 7/1994 | Walker | |
| 5,702,460 A | 12/1997 | Carls et al. | |
| 5,702,466 A | 12/1997 | Pappas et al. | |
| 5,824,105 A * | 10/1998 | Ries et al. .................. | 623/20.31 |
| 6,039,764 A | 3/2000 | Pottenger et al. | |
| 6,074,425 A | 6/2000 | Pappas | |
| 6,117,175 A | 9/2000 | Bosredon | |
| 6,123,729 A | 9/2000 | Insall et al. | |
| 6,126,693 A | 10/2000 | O'Neil et al. | |
| 6,152,960 A | 11/2000 | Pappas | |
| 6,165,222 A | 12/2000 | Hoeppner et al. | |
| 6,203,576 B1 | 3/2001 | Afriat et al. | |
| 6,206,926 B1 | 3/2001 | Pappas | |
| 6,217,619 B1 | 4/2001 | Keller | |
| 6,235,060 B1 | 5/2001 | Kubein-Meesenburg et al. | |
| 6,299,645 B1 | 10/2001 | Ogden | |
| 6,325,828 B1 | 12/2001 | Dennis et al. | |
| 6,406,497 B2 | 6/2002 | Takei | |
| 6,416,552 B1 | 7/2002 | Hoeppner et al. | |
| 6,443,991 B1 | 9/2002 | Running | |
| 6,527,807 B1 | 3/2003 | O'Neil et al. | |
| 6,540,786 B2 | 4/2003 | Chibrac et al. | |

(Continued)

FOREIGN PATENT DOCUMENTS

WO  WO 9710776 A2 *  3/1997

(Continued)

OTHER PUBLICATIONS

Raymond P. Robinson, "The Early Innovators of Today's Resurfacing Condylar Kness", Arthroplasty, vol. 20, Suppl 1, 2005.

*Primary Examiner* — Brian E. Pellegrino
(74) *Attorney, Agent, or Firm* — Kelley Drye & Warren LLP

(57) ABSTRACT

A recess-ramp knee joint prosthesis comprising a femoral and a tibial component is configured to reproduce normal kinematics and function. Asymmetric condular surfaces and a cupola of the femoral component interact with corresponding dished surfaces and a ramp of the tibia thereby duplicating the behavior of the anatomical knee.

9 Claims, 6 Drawing Sheets

U.S. PATENT DOCUMENTS

| | | |
|---|---|---|
| 6,589,283 B1 | 7/2003 | Metzger et al. |
| 6,616,696 B1 | 9/2003 | Merchant |
| 6,770,097 B2 | 8/2004 | Leclercq |
| 6,846,329 B2 | 1/2005 | McMinn |
| 6,887,276 B2 | 5/2005 | Gerbec et al. |
| 6,893,467 B1 | 5/2005 | Bercovy |
| 6,902,582 B2 | 6/2005 | Kubein-Meesenburg et al. |
| 6,962,607 B2 | 11/2005 | Gundlapalli et al. |
| 6,986,791 B1 | 1/2006 | Metzger |
| 7,025,788 B2 | 4/2006 | Metzger et al. |
| 7,264,635 B2 | 9/2007 | Suguro et al. |
| 7,326,252 B2 | 2/2008 | Otto et al. |
| 7,354,454 B2 | 4/2008 | Stack et al. |
| 7,364,590 B2 | 4/2008 | Siebel |
| 7,413,577 B1 | 8/2008 | Servidio |
| 7,497,874 B1 | 3/2009 | Metzger et al. |
| 2002/0010512 A1 | 1/2002 | Takei |
| 2002/0022889 A1 | 2/2002 | Chibrac et al. |
| 2002/0120340 A1 | 8/2002 | Metzger et al. |
| 2004/0143339 A1 | 7/2004 | Axelson et al. |
| 2004/0186582 A1 | 9/2004 | Yasuda et al. |
| 2004/0243244 A1 | 12/2004 | Otto et al. |
| 2005/0055102 A1 | 3/2005 | Tornier et al. |
| 2005/0102032 A1 | 5/2005 | Beynnon et al. |
| 2005/0209701 A1 | 9/2005 | Suguro et al. |
| 2006/0004460 A1* | 1/2006 | Engh et al. .................. 623/20.21 |
| 2006/0142867 A1 | 6/2006 | Metzger et al. |
| 2007/0135925 A1* | 6/2007 | Walker ....................... 623/20.21 |
| 2008/0140212 A1 | 6/2008 | Metzger et al. |
| 2009/0043396 A1 | 2/2009 | Komistek |

FOREIGN PATENT DOCUMENTS

| | | | |
|---|---|---|---|
| WO | WO 9820818 A1 * | 5/1998 | |

* cited by examiner

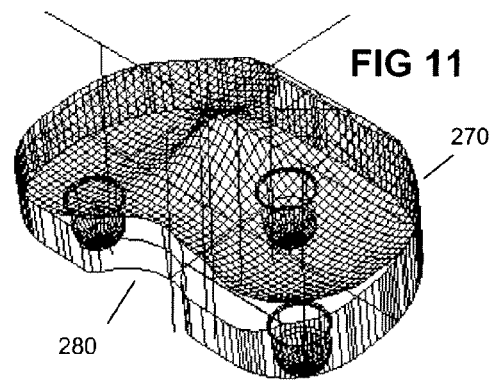
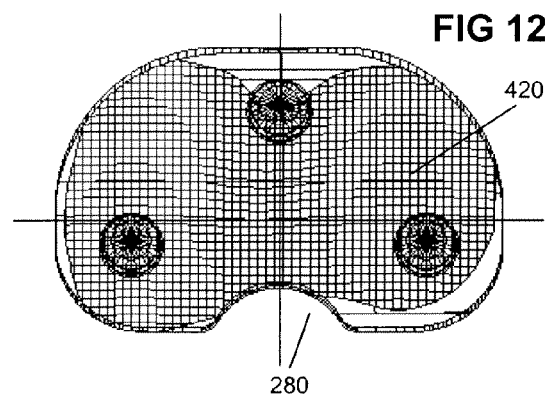
FIG 11
FIG 12
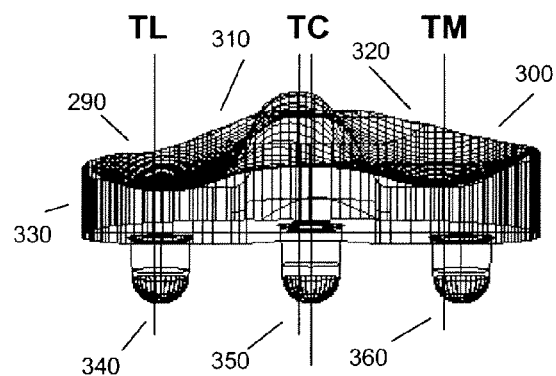
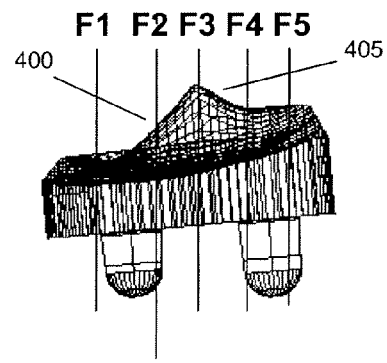
FIG 13
FIG 14
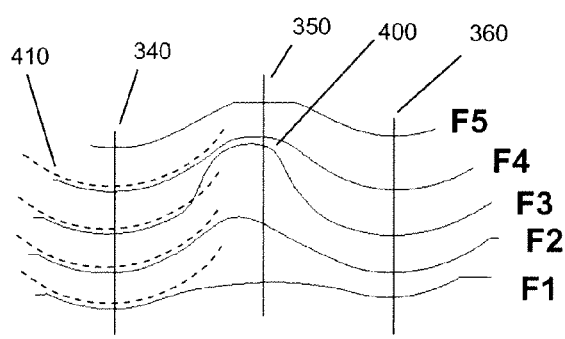
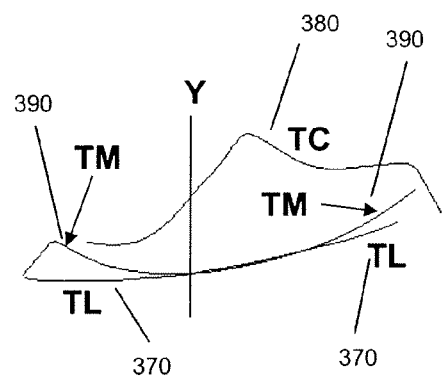
FIG 15
FIG 16

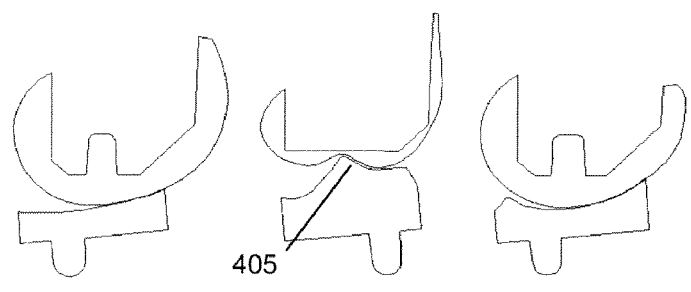
FIG 17  FIG 18  FIG 19
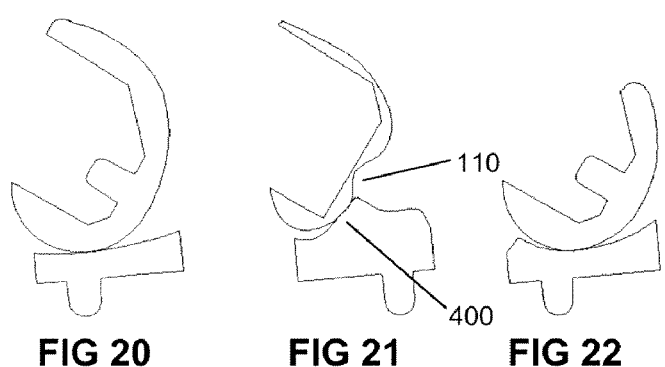
FIG 20  FIG 21  FIG 22
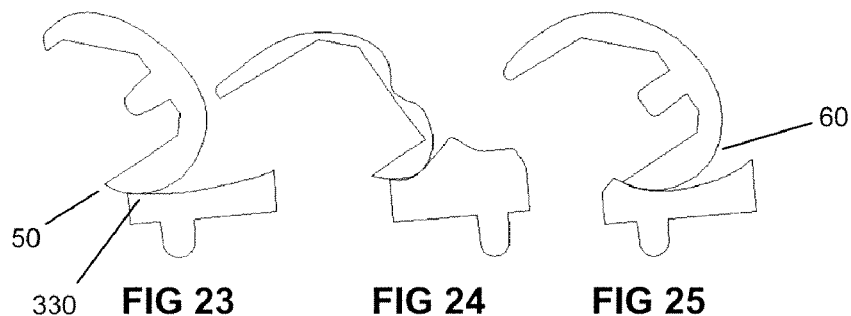
FIG 23  FIG 24  FIG 25
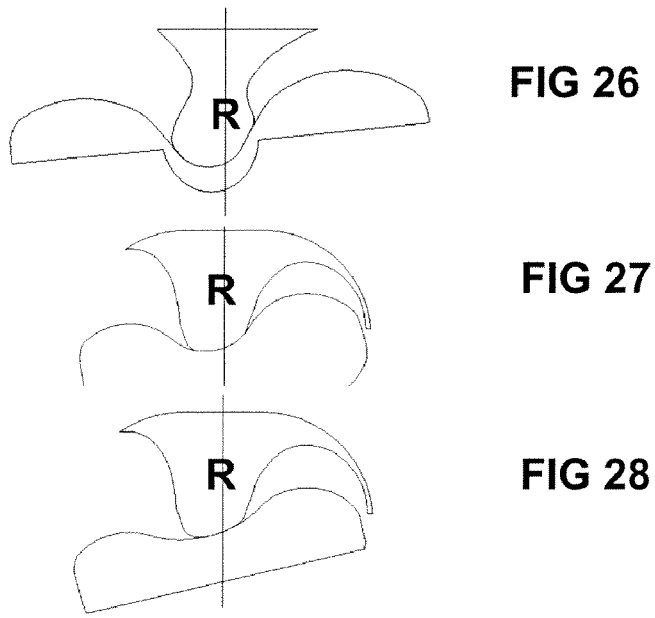
FIG 26
FIG 27
FIG 28

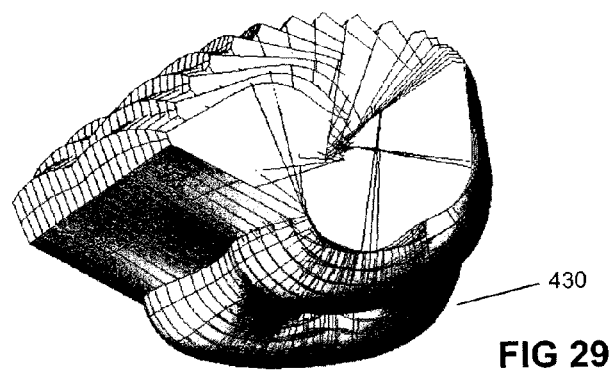
FIG 29
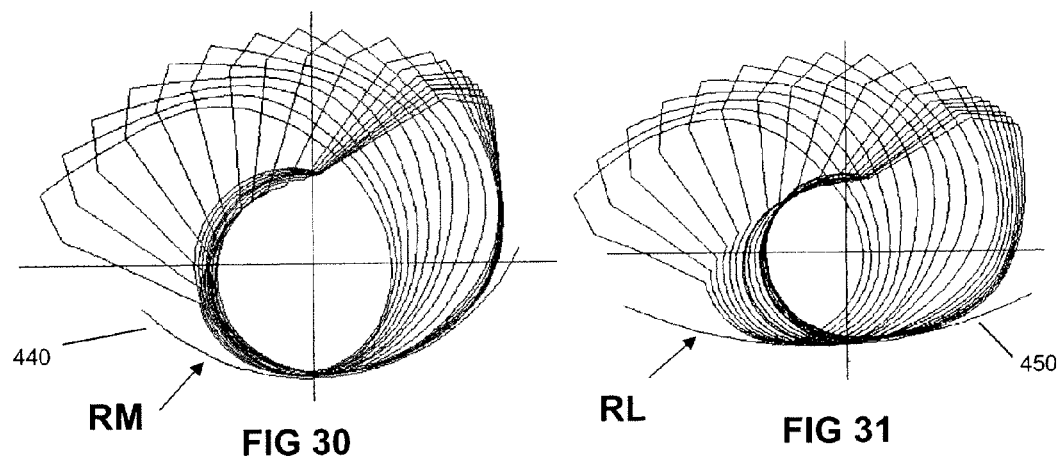
RM  FIG 30
RL  FIG 31
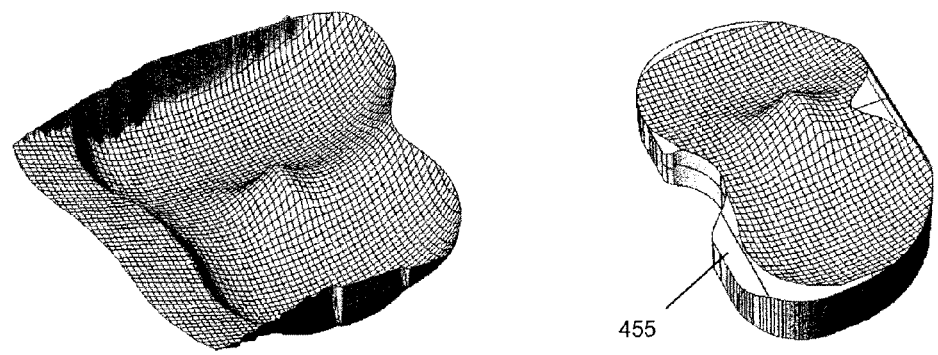
FIG 32  FIG 33

RECESS-RAMP KNEE JOINT PROSTHESIS

CROSS-REFERENCE TO RELATED DOCUMENTS

This U.S. Utility Patent Application claims priority to U.S. Provisional Patent Application 61/075,158, filed Jun. 24, 2008, and U.S. Provisional Patent Application 61/100,488, filed Sep. 26, 2008. This reference and all additional references cited in this specification, and their references, are incorporated by reference herein where appropriate for teachings of additional or alternative details, features, and/or technical background.

BACKGROUND

The term Guided Motion Knees was formulated in the mid-1990's in an effort to conceptualize features in the femoral and tibial components of a total knee replacement (TKR) which would guide the motion of the knee during flexion and extension. The particular motion characteristics of interest were those on a natural anatomic knee itself; as the knee is flexed, posterior displacement (or rollback) of the femur on the tibia, external rotation of the femur on the tibia, and rotational and anterior-posterior laxity at all angles of flexion. Guided Motion in a basic form has already been addressed in many previous designs dating back to the early 1970's, using the geometry of the lateral and medial bearing surfaces, as well as central cam-post mechanisms. (Raymond P. Robinson, *The Early Innovators of Today's Resurfacing Condylar Knees*, Journal of Arthroplasty, Vol. 20, Suppl 1, 2005). Almost all of the total knee replacements on the market today have similar shapes for the lateral and medial sides, such that there is little lateral or medial bias to the motion. However, in recent years, designs have emerged which have attempted to produce asymmetric motion. One of the first was the Medial Pivot Knee (based on early concepts by Freeman et al., Wright Manufacturing) and the Journey Knee (Smith & Nephew). The Medial Pivot Knee is based on a completely stable medial side and a rotatable lateral side. The Journey Knee has more conformity medially than laterally with a slightly convex lateral tibial surface, together with a cam-post mechanism to produce femoral rollback with flexion. There is evidence that these designs do bring knee kinematics and function closer to natural anatomic than symmetric designs. However, there continues to be a need for a total knee replacement which, more perfectly, reproduces normal kinematics and function, and feels like a natural knee.

BRIEF SUMMARY

In one embodiment of the present invention there is provided a prosthetic knee joint comprising: a tibial component comprising an asymmetric lateral dished surface and an anteriorly elevated medial dished surface, and a protrusion located between the lateral dished surface and the anteriorly elevated medial dished surface, anterior portion of the protrusion defining an anterior ramp and posterior portion of the protrusion defining a posterior ramp, the medial dished surface further comprising an external rotation axis; a femoral component comprising asymmetric lateral and medial condylar shaped surfaces, an anterior femoral groove, and a cupola located between the lateral and medial condylar surfaces, the cupola being a continuation of the femoral groove; the lateral condylar shaped surface is in sliding contact with the lateral dished surface, the medial condylar shaped surface is in sliding contact with the medial dished surface, and, for angles of flexion within a specified range, a surface of the cupola is in contact, and conformal with the posterior ramp; the lateral and the medial condylar surfaces and the posterior ramp and the surface of cupola are respectively configured to maintain contact as the lateral condylar surface displaces posteriorly, with respect to the external rotation axis, in concert with flexure.

In embodiments is additionally disclosed a prosthetic knee joint wherein the medial condylar surface and the medial dished surface, at zero degree flexure, is substantially conformal. Embodiments also comprise the lateral condylar surface and the lateral dished surface, at zero degree flexure, is substantially conformal anteriorly and non-conformal posteriorly; that the medial and the lateral condylar surfaces have arcuate sagittal profiles comprising a connected sequence of substantially circular arcs; and that the medial condylar surfaces have arcuate sagittal profiles comprising a connected sequence of substantially circular arcs, having a diminished radius relative to the arc immediately anterior; and that the cupola surfaces and the ramp surfaces are mathematically continuous and have substantially non-constant derivatives; and that the cupola surface transitions to the adjoining surface with a rounded edge having a radius of greater than 3 millimeters. Additional embodiments include that the specified range of angles of flexion extends from 30 or 60 degrees to maximum flexion. Maximum flexion is typically approximately 155 degrees.

Embodiments further include that the medial dished surface, the lateral dished surface, and the ramp are defined as surfaces conformal to an envelope of maxima of the distal femoral surfaces resulting from a succession of incremental placements of the femoral component along the desired motion track corresponding to joint flexure; and that the tibial component further comprises a ligament clearance depression in the posterior vertical wall and the femoral component further comprises a ligament clearance notch located between the condylar surfaces; and that the tibial component and femoral component comprise separable portions contained by the ligament clearance depression and the ligament clearance notch respectively.

Embodiments also include an artificial knee comprising: a first component having an outer generally J-shaped surface and an inner generally J-shaped surface: the outer generally J-shaped surface comprising a first asymmetric bilateral lobular profile comprising a first lobe and a second lobe, the first lobe having first radius, and the second lobe having a larger second radius, the first asymmetric bilateral lobular profile being adjacent to a second accurate asymmetric bilateral profile, the bilateral profiles defined by an intermediate off-center depression of non-uniform depth traversing along the generally J-shaped outer surface, the depression including, along its traverse, a pit; the inner generally J-shaped surface comprising a first lateral surface, a bottom surface and a second lateral surface, the second lateral surface being taller in height than the first lateral surface, and the bottom surface comprising a ridge extending between the first lateral surface and the second lateral surface; a second component having an upper surface, a bottom surface and a circumscribing transverse surface between the upper surface and the bottom surface: the upper surface defining a first and second dished section, asymmetric to one another, the first dished section being anteriorly elevated with respect to the second dished section and the second dished section having a shallower profile than the first dished section, and the upper surface further defining an intervening elevated section between the two dished sections, the intervening elevated section having a discrete mound component emanating therefrom, the mount having a first slope and a second opposing slope, the first slope being angled steeper than the second opposing slope; the bottom surface defining one or more protrusions from such surface, wherein the mound of the intervening elevated section of the second component is configured to fit within the pit of the first component, the first lobe of the first component is configured to fit within the first dished section of the second component and rest on a surface thereof when the mound is fit within the pit, and the second lobe of the first component is configured to fit within the second dished section of the second component and rest on a surface the reof when the mound is fit within the pit.

Definitions

Condylar shaped surface is a surface located on the distal portion of the femoral component and having the shape of an anatomic condyle.

Conformity between two curves means that the radii at the contact are nominally the same.

Cupola is a cavity or depression in the distal surface of the femur located between the medial and lateral condyles. The posterior of the cupola serves as a surface which contacts the ramp or post, protruding from the tibia, during flexion.

Cupola height is the distance between the base of the cupola and the profile of the lateral and medial femoral condyles as seen in the sagittal view.

Drape is a free-form surface which overlays a composite of surfaces without penetrating any of the surfaces.

External rotation of the femur is the rotation of the femur about an axis, located on the medial condylar surface of the tibia, which is parallel to the long axis of the tibia.

External rotation axis is the axis on the medial side of the tibia about which the external femoral rotation takes place.

Frontal plane is mutually perpendicular to the sagittal and transverse planes.

Laxity is the amount of displacement or rotation that can occur due to lack of conformity between two adjacent surfaces.

Post is a ramp with a posterior surface having a slope of greater than approximately 45 degrees.

Protrusion is a mound-like structure, projecting upward from the tibial component. The surface of the protrusion defines an anterior ramp having an average slope rising from the anterior of the protrusion toward the posterior, and a posterior ramp having an average slope rising from the posterior of the protrusion toward the anterior.

Ram is the surface of a protrusion from the proximal surface located between the medial and lateral tibial bearing surfaces. The posterior of the ramp serves as a contact surface which contacts the cupola contained portion of the femur.

Sagittal plane is a plane which divides the femur and tibia into left and right halves Transverse plane is a horizontal plane perpendicular to the long axis of the tibia.

Transverse plane projection is the geometric projection of a specified line segment onto the transverse plane.

BRIEF DESCRIPTION OF FIGURES

The following detailed description, given by way of example, will be best understood in conjunction with the accompanying drawings in which:

FIG. 11 is a perspective view of the tibial component.

FIG. 12 is a view of the tibial component on the transverse plane.

FIG. 13 is a view of the tibial component on the frontal plane.

FIG. 14 is a view of the tibial component on the sagittal plane.

FIG. 15 shows sections F1 thru F5 from the sagittal view, showing the profiles of the tibial bearing surfaces.

FIG. 16 shows sagittal sections TL, TC, and TM, from the frontal view, showing the lateral profile, the ramp profile and the medial profile.

FIGS. 17, 18, 19 show the sagittal sections through the lateral condyle, the ramp-post, and the medial condyles, at zero degrees flexion.

FIGS. 20, 21, 22 show the sagittal sections through the lateral condyle, the ramp-post, and the medial condyles, at 60 degrees flexion.

FIGS. 23, 24, 25 the sagittal sections through the lateral condyle, the ramp-post, and the medial condyles, at 120 degrees flexion.

FIG. 26 shows a section in the transverse plane through the contact area of the cupola and ramp at 60 degrees flexion.

FIG. 27 shows a section in the transverse plane through the contact area of the cupola and ramp at 90 degrees flexion.

FIG. 28 shows a section in the transverse plane through the contact area of the cupola and ramp at 120 degrees flexion.

FIG. 29 is a composite of femoral components at multiple positions in the prescribed motion path throughout the full range of flexion.

FIG. 30 is a sagittal plane view of the medial sections, corrected so that the lowest points lie on an arc RM.

FIG. 31 is a sagittal plane view of the lateral sections, corrected so that the lowest points lie on an arc RL.

FIG. 32 is a drape of the lower surface of the composite of corrected femoral components, which defines the tibial surface.

FIG. 33 is a tibial component where the surface including the bearing surfaces and ramp, is the aforementioned drape surface.

DETAILED DESCRIPTION

Figure 1:
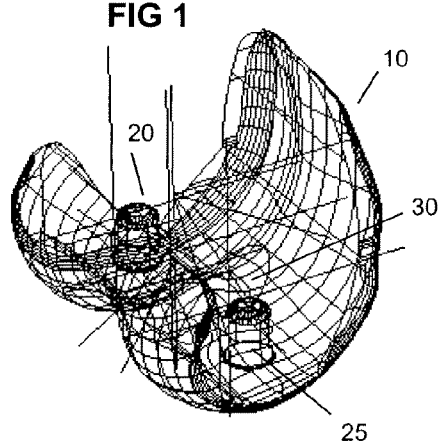
FIG. 1 is a perspective view of the femoral component.

During everyday activities, the knee joint experiences a variety of forces, including axial compressive and anterior-posterior shear, and moments, including varus-valgus and axial torque. The knee can achieve flexion angles of up to approximately 155 degrees, while the relative motions between the femur and the tibia include numerous combinations of femoral-tibial positional relationships at the bearing surfaces. Stability is essential, which is provided by a combination of bearing surface interaction, muscle forces and the soft tissues in and around the joint. There is now considerable evidence that the major anterior-posterior stability, of the femur with respect to the tibia, is derived from the medial side, which allows only a few millimeters of anterior-posterior displacement. In the anatomic knee, this stability is provided by the cruciate ligaments, together with the medial collateral ligament. The higher the compressive load, the more the stability is provided by the medial meniscus in combination with the dishing and anterior upsweep of the tibial plateau. In contrast, the lateral side of the knee is extremely mobile. During the full range of flexion, the lateral femoral condyle displaces posteriorly by about 20 mm. while the medial femoral displaces posteriorly only a few millimeters, and that only at the higher flexion angles. Hence the concept of knee mechanics is that the stability is provided by the medial side while the mobility is provided by the lateral side. This mode of function is necessary for the patient to feel that their artificial knee feels like their natural anatomic knee.

The Ramp Knee, a type of Guided Motion Knee, reproduces these mechanical properties, due to the design of the femoral and tibial bearing surfaces and the interaction of a central ramp or post on the tibial component which locates within a housing or cupola in the center of the femoral component. The cupola is blended to the surrounding bearing surfaces laterally, medially, anteriorly and posteriorly. The sagittal profiles in the centers of the lateral and medial condyles preferably resemble natural anatomic shapes. The radius of curvature of the distal sagittal profile of the medial side condyle is constant up to about 30 degrees flexion while the lateral condylar surface has a radius of curvature, at the point of tibial contact, which reduces with flexion. The depth of the femoral cupola reduces steadily from the distal end of the femur, where it can preferably be 10-15 mm in depth, to the posterior, where it becomes less than 7 mm in depth.

The respective medial and lateral tibial surfaces may be generated by mathematically superimposing multiple femoral surfaces, each of which corresponds to the correct orientation of the femur, with respect to the tibia, for a full range of flexion angles. The correct orientation of the femur may be determined to be a predefined function of the external femoral rotation and posterior displacement of the femur as a function of flexion angle based on empirical data of the neutral path of motion. The neutral path of motion is the trajectory followed by the femur, without the influence of superimposed shear or torque forces. Therefore, characterization of the orientation includes, in part, axial rotation of the femur about an external rotational axis in the tibia, together with corresponding posterior displacements of the femur on the tibia. The external rotation axis can change in position with flexion, but is within approximately 10 mm of the medial femoral-tibial contact point. The point of contact of the medial condyle and the associated external rotational axis undergoes a small displacement over the full range of flexion. A resulting surface of femoral contact is created by incrementing the flexion angle of the femur in small increments (i.e. 5 to 15 degrees) and generating a drape or envelope of the lower surfaces of the composite femoral positions.

Typically the medial side of the femur displaces 2-4 mm while the axial rotation is about 15-20 degrees, resulting in a lateral side posterior displacement of about 15-20 mm. In order to accommodate such a large lateral displacement, the transverse axis of the femur at zero degrees flexion, is rotated internally on the tibia, so that the lateral contact location is anterior to the center of the tibial plateau, resembling the screw-home mechanism of the femur on the tibia, as the femur comes into terminal extension. The lower surface of the composite envelope of the femoral surfaces, will be conformal with the tibial surface and is consistent with the required neutral path of motion. However it will be understood that for purposes of tolerances and to allow some laxity to occur, the tibial surface will be relieved slightly to avoid a tight femoral-tibial fit. In any case, laxity is inherent in this tibial surface except at the extremes of the flexion range. To produce this behavior, extra femoral surfaces can be added to provide the required laxity to the composite at the extremes.

After generating the composite femoral positions, a modification in the sagittal plane is carried out whereby the profiles are placed on arcs. On the medial side, the arc is of small radius, for example 40-50 mm, while on the lateral side, the arc is of large radius, for example 70-100 mm. The anterior parts of the arcs will preferably be of smaller radius than the posterior, to allow for a high flexion range and posterior displacement of the lateral femoral condyle in flexion. The final step is to mathematically smooth the composite of the corrected femoral surfaces, using a drape function. This resulting smoothed surface defines that portion of the tibia which is contacted by the condyles. The tibial surface also includes the central ramp or post surface which is similarly generated by the envelope of successive positions of the femoral cupola. This process results in a central ramp or post which is not as steep as a typical central post on typical PS total knees. However it will be appreciated that the steepness of the ramp will be determined by the pattern of cupola heights from the distal end of the femur to the posterior. An important feature of both the femoral and tibial surfaces is that all of the curves are continuous without corners or edges, for the purpose of avoiding stress concentrations and providing large areas of contact.

Figure 2:
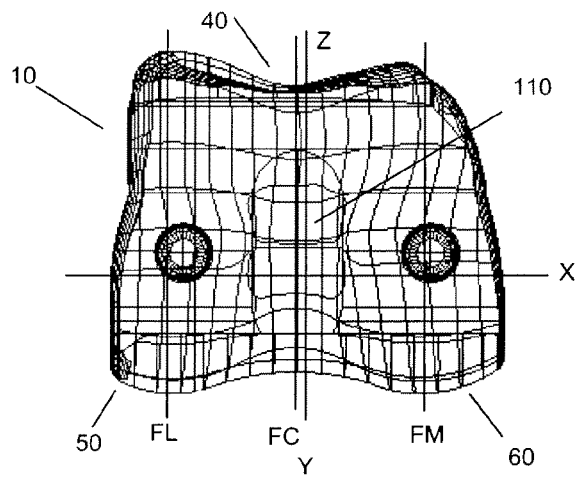
FIG. 2 is an overhead view of the femoral component on the transverse plane, with anterior above, posterior below, lateral left, and medial right.
Figure 3:
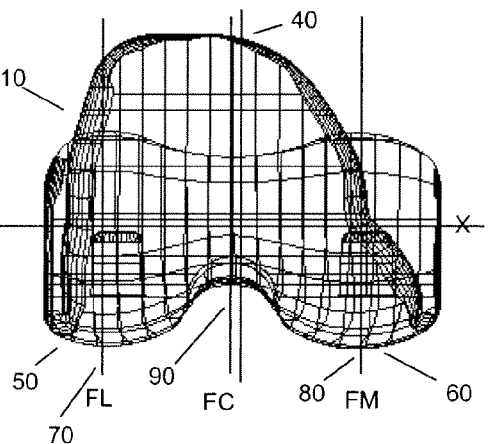
FIG. 3 is a frontal view of the femoral component on the frontal plane, with superior above and inferior below.
Figure 4:
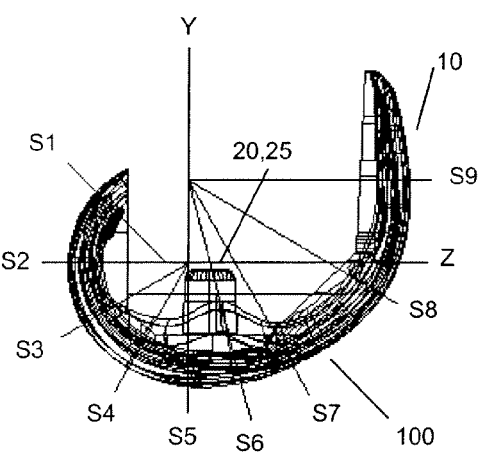
FIG. 4 is a side view of the femoral component on the sagittal plane, with anterior to the right, posterior to the left.

FIG. 1 is a perspective view of the femoral component 10, where the general peripheral shape matches an average anatomical knee shape, Two short posts 20, 25 are typically used for fixation. The upper surface of a shallow cupola 30 is seen centrally. FIG. 2 shows at the superior the typical anatomic shape of the patella groove 40 or trochlea. At the inferior, the lateral femoral condyle 50 is more prominent than the medial 60. FIG. 3 shows the frontal view, where the anterior view of the lateral and medial femoral condyles are shown. The radii are 23 mm, which blends well with the patella groove 40, and is typical of an anatomic shape. For a femoral component this radius can be increased, particularly towards the outsides of the component. FIGS. 2 and 3 show the planes of sagittal sections through the lateral femoral condyles (FL) 70, center of the cupola (FC) 90, and the medial femoral condyles (FM) 80. FIG. 4 shows the sagittal view, with anterior to the right. The two fixation posts 20, 25 can be seen. This view also shows the sections of the profiles of the condylar bearing surfaces 100, which are shown in FIG. 5.

Figure 5:
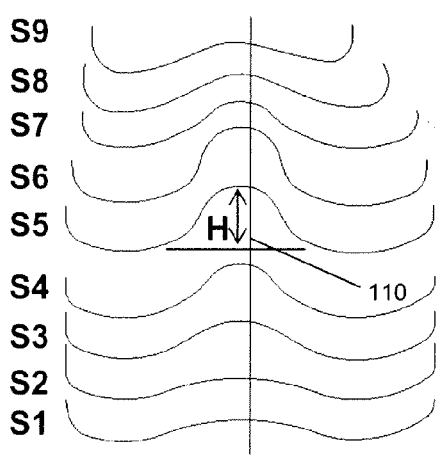
FIG. 5 shows sections S1 thru S9 from the sagittal view, showing the profiles of the femoral bearing surfaces.

FIG. 5 shows the condylar profiles around the femoral component, S1-S6 being the profiles which contact the tibial bearing surfaces, S7-S9 being on the patella trochlea. The height of the cupola H 110 is maximum in the region of profile 6, and then the height reduces around the bearing surface until it reaches a minimum at about profile S2. This can be seen more clearly in FIG. 6. The depth P130 of section S1 can be zero resulting in a cylindrical section of bearing surface running from lateral to medial. The difference between the maximum D 120 and minimum P 130 represents the height of the ramp or post on the center of the tibial component. The rate of change of heights also control the slope of the ramp or post.

Figure 6:
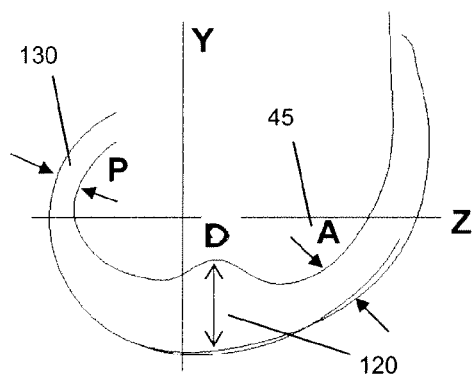
FIG. 6 shows sagittal sections FL, FC, and FM, from the frontal view, showing the lateral profile, the cupola profile and the medial profile.
Figures 7, 8:
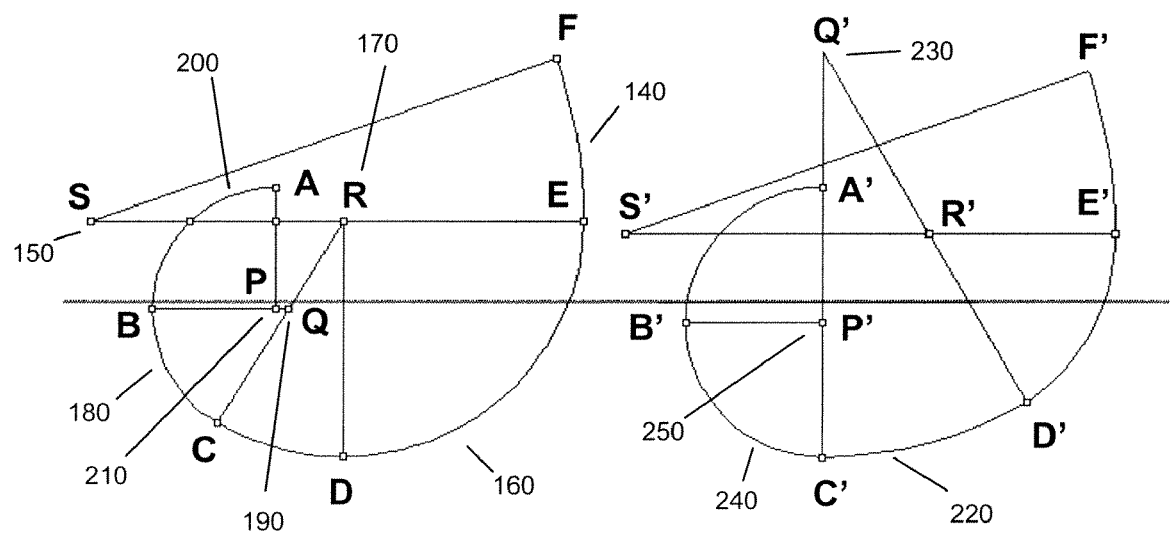
FIG. 7 shows the construction of a typical medial profile of the femoral component using circular arcs.
FIG. 8 shows the construction of a typical lateral profile of the femoral component using circular arcs.

The angle of the posterior surface of the ramp to the horizontal will usefully be in the range of 30-90 degrees. The height at section S1 will be less than or equal to the depth of the patella groove A 45 which is typically 7mm. However this may not have sufficient medial-lateral stability and hence a minimum depth of approximately 3 mm is preferable. As shown in FIGS. 6, 7, and 8, the shapes of the lateral and medial profiles are different.

Figure 9:
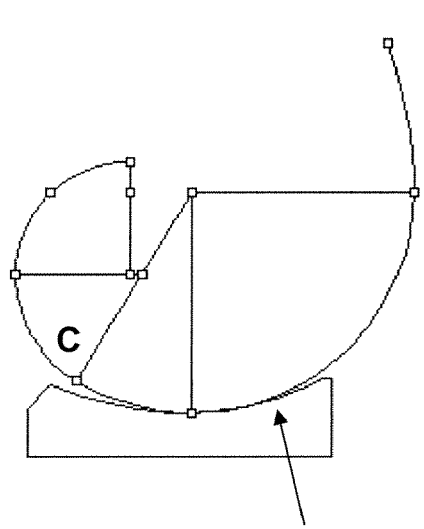
FIG. 9 shows the medial profile located on a section of the tibial bearing surface at zero degrees flexion.
Figure 10:
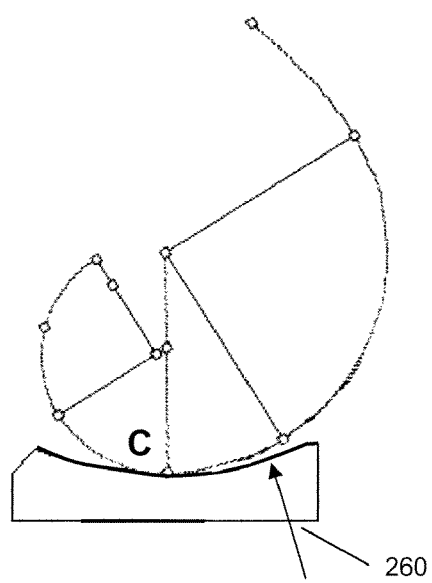
FIG. 10 shows the medial profile located on a section of the tibial bearing surface at 30 degrees flexion.

FIG. 7 shows a preferred profile of the medial bearing surface. Arc FE 140, center S 150, is the upper trochlea. From E to C 160, center R 170, is a constant radius, or close to constant. The arc CB 180, center Q 190, is reduced; and the arc BA 200, center P 210, is further reduced to facilitate a high range of flexion. FIG. 8 shows the equivalent profile of the lateral bearing surface. In this case, arc D'C' 220, center Q' 230, is much larger than arc C'B' 240, center P' 250. These profiles resemble anatomic, and many ways of describing these profiles by arcs or spirals can be accomplished while retaining the general shapes. For the medial profile, the advantage is described by FIGS. 9 and 10. At zero flexion, the femoral and tibial surfaces are close to conformity (arrow), such that anterior sliding of the femur on the tibia is restricted. When the knee flexes to 30 degrees, the sliding is still restricted 260. From 30-60 degrees, there is less restriction. However the ramp-cupola will start to act between 30-60 degrees, preventing the femur from displacing anteriorly on the tibia.

FIG. 11 shows a perspective view of the tibial component 270, with the posterior to the lower left. In the center of the face is a curved notch 280, both to fit the anatomic contour of the upper tibia, and for passage of the posterior cruciate if this is retained. The notch 280 can also be seen at the bottom of FIG. 12. FIG. 13 shows a posterior view where dished surfaces 290,300 that receive the corresponding condyles 50,60 are separated by a central protrusion. The anterior medial side 320 to the right of FIG. 13 is higher than lateral side 310 to the left. This again illustrates the differences between the more conforming medial side 300 and less conforming lateral side 290. The dished medial tibial surface 300 will restrict anterior femoral sliding. The sections TL 340, TC 350, and TM 360, are the locations of sagittal sections on the lateral side 370, ramp 380, and medial side 390, shown in FIG. 15. In FIG. 14, the slope of the posterior ramp 400 and the slope of the anterior ramp 405 is seen. In this case the slope of the posterior ramp is 45 degrees, but various slopes are possible. A shallower slope will provide less definitive motion guidance, while a steeper slope will generally require a higher cupola, a disadvantage in regard to removal of bone when fitting to the femur. F1-F5 are the locations of frontal plane sections, shown in FIG. 16.

In FIG. 15, the frontal radii of the lateral and medial bearing surfaces are shown. Except for the extreme anterior section F5, the frontal radii are constant from anterior to posterior, shown with the dashed arcs 410. However, towards the posterior, F1, the arc radius is the same but the arc length is reduced because of the reduced central height. The advantage of the constant radius is that there can be close conformity of the tibial bearing surface with the femoral bearing surface throughout the entire flexion range, minimizing contact stresses. In this figure, it can be seen that the posterior ramp 400 is disposed approximately 2 mm to the lateral side, to match the cupola 110 seen in FIG. 5, this feature of a lateral shift being anatomic.

FIG. 16 shows a comparison between the sagittal profiles of the lateral TL 370 and medial TM 390 bearing surfaces. The medial is more dished both anteriorly and posteriorly to provide anterior-posterior stability, although the femoral radius is larger in order to allow 2-4 mm of anterior-posterior laxity, especially in high flexion. The lateral profile is shallow anteriorly to allow internal femoral rotation in extension, the so-called screw-home mechanism, and posteriorly to allow posterior displacement of the lateral femoral condyle in flexion.

FIGS. 17-20, respectively show the lateral, central and medial sections at zero degrees flexion. The low lateral conformity and high medial conformity have already been described. The anterior ramp 405 now acts to limit extension, although rocking is possible to allow up to 5 degrees of hyperextension. FIGS. 20-22 show the sections at 60 degrees flexion. Here, the posterior ramp 400 and cupola 110 is seen to be in contact. The ideal initial contact is in the range of 30-60 degrees flexion. Finally, FIGS. 23-25 show the sections at 120 degrees flexion. The lateral femoral condyle 50 is posterior on the tibial surface 330, while the medial femoral condyle 60 has displaced 2-4 mm, these actions due to the posterior ramp 400 and cupola 10 and the relative dishing of the lateral 290 and medial 300 sides. Due to the differential displacements, the femoral component has rotated approximately 20 degrees externally about an axis 420 on the medial side of the medial tibial bearing surface. During rotation, the location of axis 420 may minimally displace within the medial tibial bearing surface. Such minimal displacement may, for example, be limited to less than approximately 5 millimeters.

FIG. 26 shows a section in the transverse plane of the cupola 110 and the posterior ramp R 400, at 60 degrees flexion. The interior of the cupola is rounded, and so is the posterior surface of the ramp, such that there is close conformity, which maximizes the contact area and minimizes the contact stresses. The same situation occurs at 90 degrees flexion (FIG. 27) and 120 degrees flexion (FIG. 28). This conformal contact is a major advantage in protecting the ramp, or post, from edge damage.

FIGS. 29-33 show one method for generating surface of the tibial component 270. A composite is made of the femoral components at increments of flexion (FIG. 29). The motion path is described by simple empirical equations which describe the axial rotation and the posterior displacement of the femoral component 10 on the tibial component 270. In our case we use 20 degrees of external rotation and 4 mm of posterior displacement. However there are many values which will produce similar tibial component shapes and which would function satisfactorily. FIGS. 30 and 31 show that the sagittal sections are aligned on arcs RM 440 medially and RL 450 laterally. The radii of the arcs have been determined in previous studies of knee replacements to provide the correct combinations of stability and laxity. A drape function over the lower part of the composite of femoral components produces a surface which will replicate the combined motions of the femur, as shown in FIG. 32. It will be appreciated that the tibial surface is modified to avoid an exact fit with the femoral component. This can be done by building in small side-to-side laxity movements in the femoral composites. The final tibial component 270 is thus generated (FIG. 33) and completed by making a posterior notch 280, and relieving the posterior of the medial side with a 45 degree chamfer to avoid impingement with the posterior femoral cortex in high flexion.

Figure 34:
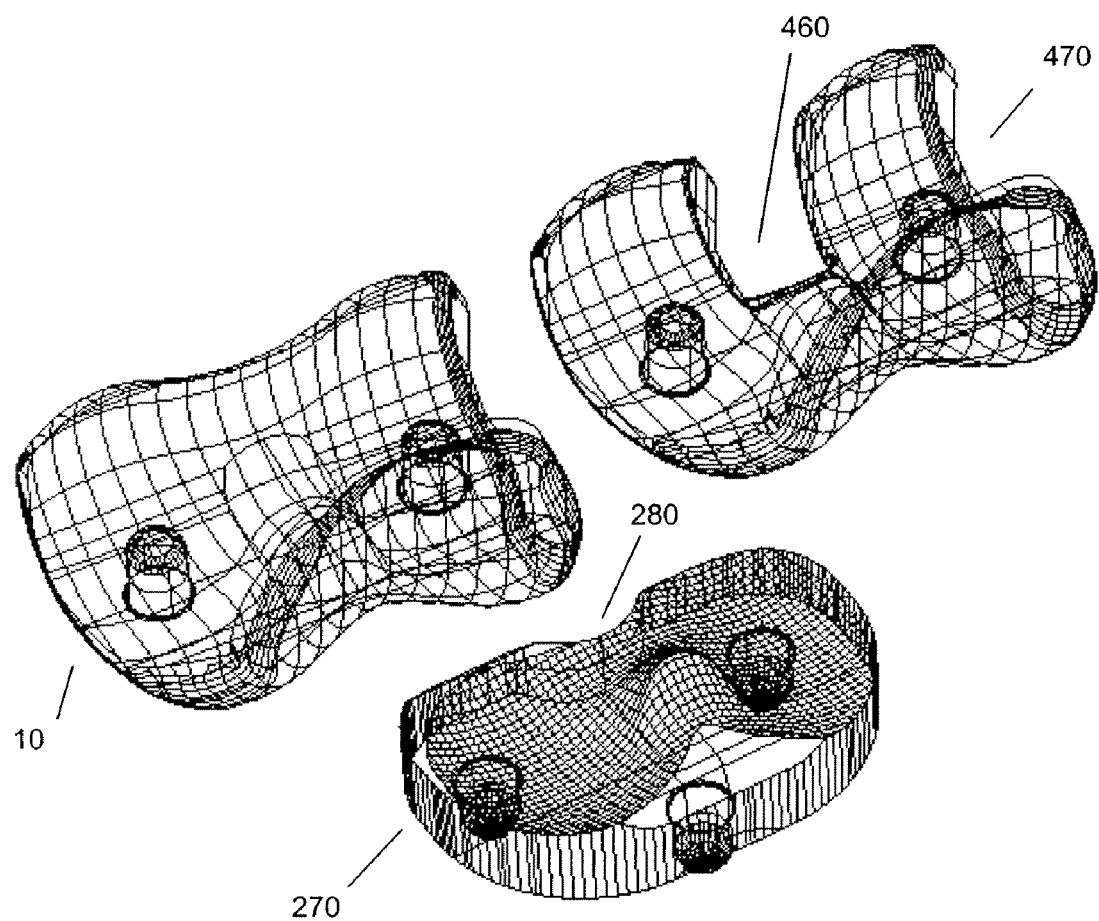
FIG. 34 shows two femoral components, the left being intended for resection of the cruciate ligaments, and the right being intended for retention of the posterior cruciate, together with a tibial component below which can be used with either femoral component.

FIG. 34 shows a convenient combination of components which can be made. The standard femoral component 10 and tibial component 270 as described thus far are shown on the left. However there are many surgical cases where it is preferred to retain the posterior cruciate ligament. To accommodate this, a slot or ligament clearance notch 460 is made in the femoral component 470. The posterior notch or ligament clearance depression 280 on the tibial component 270 allows passage of the posterior cruciate as stated already. The ramp does not interfere with motion of the cruciate retaining femoral component. However there is now no cupola to interact with the ramp and provide the posterior displacement. This function is now carried out by the posterior cruciate ligament. In an embodiment, the ligament clearance depression and ligament clearance notch may be formed by removal of separable portions of the respective tibial and femoral components.

Statement Regarding Preferred Embodiments

While the invention has been described with respect to preferred embodiments, those skilled in the art will readily appreciate that various changes and/or modifications can be made to the invention without departing from the spirit or scope of the invention, in particular the embodiments of the invention defined by the appended claims. All documents cited herein are incorporated in their entirety herein.

What is claimed is:

1. A prosthetic knee joint comprising:
    a single piece tibial component comprising a concave lateral dished surface defining a first arc projected onto a sagittal plane and a concave medial dished surface, comprising an external rotation axis and anteriorly elevated with respect to said lateral dished surface, said concave medial dished surface defining a second arc projected onto the sagittal plane wherein said first arc has a greater radius then said second arc, and posterior portions of said concave lateral dished surface and said concave medial dished surface each defined by single arcs of constant radius projected on a frontal plane, said single piece tibial component further comprising a protrusion located between said lateral dished surface and said medial dished surface, anterior portion of said protrusion defining an anterior ramp and posterior portion of said protrusion defining a posterior ramp;
    a single piece femoral component comprising lateral and medial condylar shaped surfaces, an anterior femoral groove, and a cupola located between said lateral and medial condylar surfaces, said cupola being a continuation of said femoral groove;
    said lateral condylar shaped surface in sliding contact with said lateral dished surface and operatively configured to posteriorly displace a first distance, with respect to said lateral dished surface, in response to increasing flexure, said medial condylar shaped surface is in sliding contact with said medial dished surface and operatively configured to displace a second distance lesser than said first distance, with respect to said medial dished surface, in response to increasing flexure, wherein said displacements result in rotation of said femoral component with respect to said tibial component about said external rotation axis.

2. The prosthetic knee joint, in accordance with claim 1, wherein a portion of said medial condylar shaped surface in contact with said medial dished surface is conformal, at zero degree flexure.

3. The prosthetic knee joint, in accordance with claim 1, wherein a portion of said lateral condylar shaped surface in contact with said lateral dished surface, at zero degree flexure, is conformal anteriorly and non-conformal posteriorly.

4. The prosthetic knee joint, in accordance with claim 1, wherein said medial and said lateral condylar shaped surfaces have arcuate sagittal profiles comprising a connected sequence of substantially circular arcs.

5. The prosthetic knee joint, in accordance with claim 4, wherein said connected sequence of substantially circular arcs each has a diminished radius relative to the arc immediately anterior.

6. The prosthetic knee joint, in accordance with claim 1, wherein said cupola surfaces and said ramp surfaces are mathematically continuous and have non-constant derivatives.

7. The prosthetic knee joint, in accordance with claim 1, where in said cupola surface transitions to the adjoining surface with a rounded edge having a radius of greater than 3 millimeters.

8. The prosthetic knee joint, in accordance with claim 1, wherein said medial dished surface, said lateral dished surface, and said ramp are defined as surfaces conformal to an envelope of maxima of the distal femoral surfaces resulting from a succession of incremental placements of said femoral component along the desired motion track corresponding to joint flexure.

9. The prosthetic knee joint, in accordance with claim 1, wherein:
    said tibial component further comprises a ligament clearance depression in the posterior vertical wall; and
    said femoral component further comprises a ligament clearance notch located between said condylar surfaces.

* * * * *